United States Patent [19]

Ziegenhain et al.

[11] 4,443,634
[45] Apr. 17, 1984

[54] REMOVAL OF IMPURITIES

[75] Inventors: William C. Ziegenhain; Gary L. Horton, both of Ponca City, Okla.

[73] Assignee: Conoco Inc., Ponca City, Okla.

[21] Appl. No.: 480,178

[22] Filed: Mar. 29, 1983

[51] Int. Cl.$^3$ ............................................. C07C 41/34
[52] U.S. Cl. .................................................. 568/621
[58] Field of Search ........................................ 568/621

[56] References Cited

U.S. PATENT DOCUMENTS

| | | | |
|---|---|---|---|
| 2,346,783 | 4/1944 | Plewes | 568/621 |
| 3,299,151 | 1/1967 | Wismer et al. | 568/621 |
| 3,357,970 | 12/1967 | Wyatt | 568/620 |

*Primary Examiner*—Howard T. Mars
*Attorney, Agent, or Firm*—Robin M. Davis

[57] ABSTRACT

This purification process has been developed for liquid polymer feed streams having one or more impurities present at levels of 2% or less by weight of the stream. This purification process comprises: (a) forcing the liquid polymer feed stream through a spray nozzle into an inert atmosphere at a temperature of from about 68° F. to about 392° F. where the pressure is at or below 1 atmosphere in such a manner to atomize the feed stream into particulate drops having a size in the range of from about 1,000 microns to about 50 microns in diameter, (b) retaining particulate drops under the conditions of (a) and at a temperature in the range of from about 68° F. to about 392° F. for at least 0.10 seconds to form impurity vapors, (c) removing the vaporous impurities that form during step (b), and (d) collecting the purified atomized feed stream liquid wherein the purified feed stream has a vapor pressure no higher than $1 \times 10^{-3}$ (mm) of mercury (Hg) at 68° F. and no higher than 50 mm of Hg at 392° F., and the impurities removed in step (c) have vapor pressures no lower than 10 mm Hg at 68° F., and no lower than 5,000 mm of Hg at 392° F.

7 Claims, No Drawings

REMOVAL OF IMPURITIES

BACKGROUND AND FIELD OF THE INVENTION

Toxic and carcinogenic impurities must be removed from their polymer product streams as completely as possible. Processes which can reduce such materials to minute levels are extremely desirable; moreover, inexpensive and simple methods for removing any impurity that is present in an amount of about 2% by weight of the polymer product stream, and reducing such an impurity to less than 0.5 parts per million (ppm) is particularly desirable.

A variety of methods have been developed in the art for the purpose of controlling impurity concentration in product streams. In producing alcohol ethoxylate for example, process controls are used to maintain a low level of ethylene oxide in the product stream. These operating procedures, however, reduce production rates for the alcohol ethoxylate. Moreover, in spite of process controls during production of the alcohol ethoxylate, ethylene oxide concentration levels can reach undesirable levels.

A known purification method is described in U.S. Pat. No. 3,000,963, relating to a process for refining crude polymers and adducts of propylene oxide. This patent describes a method of reducing impurities by neutralization, filtering, and then vacuum stripping. Another purification method is noted in U.S. Pat. No. 3,357,970, relating to ethoxylation of solid polyols. The purification method used in this reference is stripping with a nitrogen purge at 392° F. under vacuum.

Spraying techniques have been used commercially for materials that are easy to separate. In the manufacture of alumina ($Al_2O_3$), for example, solid alumina is separated from liquid by-product using a spray-drier. Other commercial processes applying spray techniques are used to separate materials such as solvents which are extremely volatile, and present in feed streams in large concentrations, (over 10% by weight of the total stream).

U.S. Pat. No. 2,346,783 teaches the use of spray nozzles which relates to the purification of ethers of diethylene glycol to increase the surface area between contacting phases. Purification is achieved via extraction, taking advantage of the higher solubility of the impurities in the contacting phase.

While known purification methods can succeed in removing more volatile impurities from a product stream, disadvantages inherent to such systems include expense, time consumption, low product output, production of other impurities, loss of desirable product, lack of efficiency and consumption of great amounts of energy.

It is also difficult, if not impossible, to significantly lower the concentration of impurities having vapor pressures near the vapor pressures of the feed stream material itself. Methods which heretofore have been used to separate volatile impurities from nonvolatile or solid materials are not suitable for the removal of impurities such as dioxane from feed streams such as alcohol alkoxylate.

It would be advantageous to provide a method that can remove impurities which are present in feed streams in small quantities. The present invention provides a method for removing impurities present in concentrations less than 2% by weight of the liquid feed stream from liquid polymer feed streams having maximum volatility levels to extremely low levels. This process is especially suited for impurities present in low concentrations. The present invention is particularly useful in dioxane removal from alcohol alkoxylates.

SUMMARY OF THE INVENTION

A process for the purification of liquid polymer feed streams containing one or more impurities present in a quantity of less than 2% by weight of the stream per impurity comprises: (a) forcing the feed stream through a spray nozzle into an inert atmosphere at a temperature of from about 68° F. to about 392° F. where the pressure is at or below one atmosphere in such a manner to atomize the feed stream into particulate drops having a size in the range of from about 1,000 microns to about 50 microns in diameter, (b) retaining the particulate drops under the conditions of (a), and within a temperature in the range of from about 68° F. to about 392° F. for at least 0.10 second to form impurity vapors, (c) removing the impurity vapors that form during step (b), and (d) collecting the purified, atomized feed stream liquid, wherein the purified feed stream has a vapor pressure no higher than $1 \times 10^{-3}$ millimeters of mercury (mm of Hg) at 68° F. and no higher than 50 mm of Hg at 392° F., and the vapor pressure of any impurity removed in step (c) is no lower than 5,000 mm of Hg 392° F. and no lower than 10 mm of Hg at 68° F.

The term "liquid polymer", is hereby defined as a product of a polymerization reaction, and is in the liquid state. In fact, in order to be purified through the process of the instant invention, the polymer must be a liquid under the condition maintained.

This process is especially suited for the removal of an impurity when the impurity is present in any concentration of less than 2% by weight of the liquid polymer product stream. Such an impurity can be removed with less expense, in less time, and more completely than it can be done using known methods. This is particularly advantageous with liquid polymer feed streams having toxic and carcinogenic impurities such as 1-4,dioxane, and ethylene oxide.

Conversion of the feed into a spray increases the surface area of the liquid polymer feed stream and allows purification to take place without using large quantities of purifying gas. Moreover, with the particulate nature of the stream and minimum residence time, impurity molecules more readily enter the gaseous phase. When the proper pressure and temperature conditions are maintained, specific impurities can be induced into the gaseous phase in large percentage quantities of their total concentration in the liquid polymer product stream. If additional factors such as inert gas purging or repeated treatments are added to this process, even further reduction in impurity concentration is possible.

It is important that the impure liquid stream be sprayed into an inert atmosphere so that no reactions occur causing discoloration or more impurities. The presence of oxygen, for example, is particularly undesired.

The use of the instant invention provides the capability of removing impurities present in the liquid polymer feed streams. Under preferred conditions the concentrations of such impurities can be reduced to less than 0.5 parts per million (ppm). Moreover, this can be done with only a small amount of waste of the product stream.

DETAILED DESCRIPTION

This process is described by categorizing its parameters. The categories used are: variables affecting the impurities found in the feed stream, and variables relating to and affecting the liquid polymer feed stream.

Variables which affect the impurities present in the liquid polymer feed stream are: the minimum necessary volatility and the environmental impurity vapor concentration.

The minimum necessary volatility level which this process requires of any impurity that is to be removed, sets the vapor pressure sufficiently above the vapor pressure of the purified polymer so that purification can take place. Conveniently the volatility limits are set at 68° F. and 392° F. in terms of vapor pressure. Generally, an impurity which may be removed from the polymer stream with this process must have a minimum vapor pressure of about 10 mm of Hg at 68° F., and about 5,000 mm of Hg at 392° F.

A second variable affecting the removal of the impurities from the liquid polymer feed stream is the concentration of impurity vapors in the spray chamber. When the impure liquid polymer feed stream is sprayed into an environment of low impurity vapor concentration, a greater concentration of impurities will be removed from the liquid feed. Thus, mass transport of vaporous impurities from the spray environment is important. Impurity vapor concentration may be reduced to a minimum in the environment of the spray by maintenance of reduced pressure, an inert gas purge, or by direct removal of impure vapors.

Reduced pressure in the spray chamber will enhance the vaporization of impurities into the gaseous state, although for the more volatile impurities, reduced pressure might not be necessary, especially if temperatures in the range of from about 248° F. (120° C.) to about 392° F. (200° C.) are used. Pressure can be maintained at less than 1 atmosphere; a preferable range, however, is from about 0.5 mm of Hg (absolute) to about 300 mm of Hg (absolute); and the most preferred range is from about 1.0 to about 100 mm of Hg (abs.). Maintenance of reduced pressure in the spray chamber serves to both increase removal of impurities from the feed stream and to slightly reduce the need for higher temperatures.

Impurity vapors can also be removed by an inert gas purge. This can be combined with reduced pressure, and high temperatures if desired. A suitable range for the rate of the gas purge is from about 0.1 volume of gas/volume liquid feed to about 100 volume of gas per volume of liquid feed. A preferred range of inert gas flow is from about 0.01 to about 5.0 volumes of purge gas/volume of liquid feed. Any gas which is inert to the system is suitable as a gas purge. The choice of which gas to use will depend on individual circumstances. Representative but nonexhaustive examples of suitable inert gases are: nitrogen, helium and argon.

Representative but nonexhaustive examples of impurities with suitable vapor pressures which can be removed from the feed streams using the present invention include ethylene oxide, propylene oxide, dioxane, water, and alcohol. Using this process individual concentrations of such impurities can be reduced to less than 0.5 parts per million or most preferably, to less than 0.1 part per million.

Variables relating to the polymer feed stream itself are: volatility, temperature, feed flow rate, particle size, and sequential sprayings. While control over parameters such as temperature, feed flow rate, particle size, and sequential sprayings result in optimization of impurity removed, volatility is the determinant factor controlling the makeup up of the feed.

Conveniently, the vapor pressures at each extreme of the temperature range (at 68° F., e.g., 20° C. and a 392° F. e.g., 200° C.) are used to determine the suitability of the feed stream materials and the impurities for the process of the instant invention. Generally any material having a maximum vapor pressure of $1\times10^{-3}$ mm of mercury (Hg) at 68° F., and a maximum of 50 mm of (mercury) Hg at 392° F. is suitable. The preferred feed stream material is a liquid polymer having a vapor pressure below each maximum limit, and is made from one or more monomers at least one of which is selected from the group consisting of ethylene oxide and propylene oxide. In accordance with the instant invention any impurity removed from these streams must have vapor pressures no lower than 10 mm of Hg at 68° F., and no lower than 5,000 mm of Hg at 392° F. Thus volatility levels are set for both the feed stream and the impurities to be removed from it so that appropriate separation, is achieved, resulting in purification of the stream.

Temperature, another variable, should be maintained in the range of from about 68° F. to about 392° F. The most preferred range, however, is in the higher temperature range of from about 248° F. to about 392° F.

Particle size of the sprayed feed stream can also be controlled. The feed stream to be purified is sprayed through a nozzle while being maintained at the selected temperature. The nozzle employed and the manner of spraying should be sufficient to insure that the average particle size of the sprayed feed stream droplets is less than 1,000 microns in diameter. Preferably the sprayed feed stream droplets should be in the range of from about 1,000 microns to about 50 microns in diameter, although the average sprayed particle size can be less than 50 microns in diameter if a de-mister is used in the system.

The rate at which the feed stream progresses through the system, from and including the point of spraying to and including the point of collection, does have a major effect on the extent of purification. As the rate of progression of the feed stream through the system decreases, impurity removal increases. Generally, the feed should progress through the system at a rate sufficiently slow that the average particle residence time from the point of spraying to the point of collection should be a minimum of 0.10 second. Residence time can be controlled and increased by increasing the particle path length thus increasing the distance that each particle falls. A suitable average particle residence time is 5 seconds. It should be kept in mind, however, that variation of other operating conditions such as temperature, average particle size, or using sequential sprayings could provide comparable purification capabilities while at the same time enable a more effective use of production time.

Subjecting the feed stream to two or more sequential sqrayings instead of just one spraying is extremely beneficial. Such sequential sprayings can optimize purification and provide an opportunity to relax other extreme conditions.

When a system is maintained in accordance with the instant invention and the purification process operated carefully, impurities can be removed efficiently and effectively. Another advantage obtained is the fact that very little feed stream material is lost. Additionally, however, it should be noted that the quantities of impurities removed from the feed stream may be collected and separated into their component parts.

The process of the instant invention is more concretely described with reference to the examples below wherein all parts and percentages are by weight unless otherwise specified. The example is provided to illustrate the present invention and not to limit it.

EXAMPLE 1

A spray chamber was constructed having a spray nozzle, temperature and pressure control, and a nitrogen gas purge. The spray nozzle used was obtained from Spraying Systems Co. (atomizing No. ¼ LN1). Cold traps using dry ice and acetone were utilized to trap votatile components accumulating in the chamber. Alcohol ethoxylate feed containing known amounts of 1,4-dioxane and ethylene oxide were fed through the spray nozzle in 2,000 gram (g) quantities. Several runs were made and the following data (Table 1) was collected.

The alcohol portion of the alcohol ethoxylate feed contained $C_{12}$ to $C_{14}$ alcohol. The feed was sprayed into particulate drops in the range of from about 50 to about 1,000 microns (or having an average size of 100–200 microns), and had a residence time greater than one second for each run. Impurity analysis was conducted by gas chromatograph analysis and was accurate to ±0.2 ppm of either component.

TABLE 1

FEED ALCOHOL ETHOXYLATE
($C_{12-14}$ ALCOHOL, 60% BY WEIGHT $C_{12}$)
Single Stage Runs With The Original Feed Having 2.69 PPM
Ethylene Oxide and 2.7 PPM 1,4-Dioxane

| Sample No. | Chamber P, mm Hg | Feed ~T,°F. | EO, ppm | Dioxane, ppm |
|---|---|---|---|---|
| Feed | — | — | 269 | 2.7 |
| 1 | 1.8–6 | 184 | 28 | 2.5 |
| 2 | 8–8.5 | 177 | 28 | 2.5 |
| 3 | 45–47.2 | 169 | 44 | 3.3 |
| 4 | 97–100 | 169 | 49 | 2.8 |
| 5 | 1.5–3.2 | 259 | 8 | 0.96 |
| 6 | 4.5–10 | 255 | 21 | 1.9 |
| 7 | 45–50 | 253 | 20 | 1.5 |
| 8 | 95–100 | 250 | 29 | 2.9 |
| 9 | 1.7–3.5 | 340 | 3 | 0.65 |
| 10 | 8.9 | 354 | 7 | 1.3 |
| 11 | 45–50 | 337 | 14 | 1.5 |
| 12 | 95–100 | 345 | 28 | 1.6 |
| 13 | 1.8–4 | 255 | 7 | 0.74 |
| 14 | 45–50 | 254 | 21 | 1.8 |
| 15 | 95–100 | 254 | 29 | 2.1 |

EO - ethylene oxide

TABLE 2

SINGLE STAGE RUNS WITH THE ORIGINAL
FEED HAVING 12263 PPM ETHYLENE OXIDE,
AND 3.1 PPM 1,4-DIOXANE

| Sample No. | Chamber P, mm Hg | Feed ~T,°F. | EO, ppm | Dioxane, ppm |
|---|---|---|---|---|
| 1 | 84–88 | 348 | 48 | 3.2 |
| 2 | 48–50 | 345 | 19 | 2.3 |
| 3 | 3.5–4 | 358 | 5 | 1.8 |

EXPLANATION FOR TABLES 1 AND 2

Tables 1 and 2 show the degree of purification of the alcohol ethoxylate feed stream after one spraying under conditions stated which were set within the limits of the instant invention. Ethylene oxide is more volatile than dioxane, and larger amounts of it can be removed under less extreme conditions. By comparing conditions of certain samples, the relative effects of pressure and temperature can be ascertained. By comparing sample No. 7 and 11 of Table 1, for example, one can see that mere increase in temperature was sufficient to increase removal of ethylene oxide. The overall data indicates, however, that dioxane which is much less volatile, requires low pressure in addition to high temperatures in order to achieve its removal in large quantities.

Reproductability of the process may be observed by comparing the results from 13, 14, and 15 of Table 1 with 5, 6, and 7 of that same table.

EXPLANATION FOR TABLES 3 THROUGH 6

Effort was made to maintain similar temperature and pressure conditions over stages 1, 2, and 3, in each run in all experiments shown over Tables 3 through 6. These tables show that sequential sprayings can be used to achieve the preferred degree of purification. Moreover, certain other conditions such as temperature do not have to be maintained at such extreme levels when sequential sprayings are used. Alternatively, however, an increase in residence time of the spray will also operate to eliminate the necessity of one or more stages.

TABLE 3

MULTIPLE STAGE RUNS FEED HAVING
269 PPM ETHYLENE OXIDE
AND 1 PPM 1,4-DIOXANE IMPURITIES

| Sample No. | Chamber P, mm Hg | Feed ~T,°F. | Stage | EO, ppm | Dioxane, ppm |
|---|---|---|---|---|---|
| (Feed) | — | — | — | 269 | 1 |
| Run 1 Stage 1 | 1.8–3.0 | 281 | 1 | 5.7 | 0.3 |
| Run 1 Stage 2 | 1.5–1.9 | 275 | 2 | 0.4 | <0.1 |
| Run 1 Stage 3 | 1.5–1.8 | 279 | 3 | 0.1 | nd |
| (Feed) | — | — | — | 269 | 1 |
| Run 2 Stage 1 | 1.4–2.4 | 316 | 1 | 1.3 | 0.19 |
| Run 2 Stage 2 | 1.5–2.0 | 311 | 2 | 0.4 | nd |
| Run 2 Stage 3 | 1.6–2.0 | 305 | 3 | <0.1 | nd |
| (Feed) | — | — | — | 269 | 1 |
| Run 3 Stage 1 | 1.8–5.0 | 331 | 1 | 3.8 | .26 |
| Run 3 Stage 2 | 1.8–2.0 | 335 | 2 | 0.1 | 0.12 |
| Run 3 Stage 3 | 1.8–2.0 | 335 | 3 | <0.1 | nd | nd - nondetectable

TABLE 4

MULTIPLE STAGE RUNS HAVING 269 PPM
ETHYLENE OXIDE AND 1.2 PPM 1,4-DIOXANE

| Sample No. | Chamber P, mm Hg | Feed ~T,°F. | Stage | EO, ppm | Dioxane, ppm |
|---|---|---|---|---|---|
| (Feed) | — | — | — | 269 | 1.2 |
| Run 1 Stage 1 | 1.3–2.5 | 280 | 1 | 7.1 | <0.1 |
| Run 1 Stage 2 | 1.4–1.8 | 280 | 2 | 0.8 | 0.1 |
| Run 1 Stage 3 | 1.4–1.7 | 283 | 3 | 0.1 | nd |
| (Feed) | — | — | — | 269 | 1.2 |
| Run 2 Stage 1 | 1.4–3.0 | 303 | 1 | 2.9 | nd |
| Run 2 Stage 2 | 1.4–1.8 | 307 | 2 | 0.2 | nd |
| Run 2 Stage 3 | 2.5–4.5 | 305 | 3 | <0.1 | nd |
| (Feed) | — | — | — | 269 | 1.2 |
| Run 3 Stage 1 | 1.5–3.5 | 335 | 1 | 2.6 | nd |
| Run 3 Stage.2 | 1.5–1.8 | 336 | 2 | 0.1 | nd |
| Run 3 Stage 3 | 1.4–1.7 | 341 | 3 | <0.1 | nd |

TABLE 5

THE FEED HAVING 269 PPM ETHYLENE OXIDE AND 1.2 PPM DIOXANE IMPURITIES

| Sample No. | Chamber P, mm Hg | Feed ~T,°F. | Stage | EO, ppm | Dioxane, ppm |
|---|---|---|---|---|---|
| (Feed) | — | — | — | 269 | 1.2 |
| Run 1 Stage 1 | 10.0-11.0 | 278 | 1 | 25 | 0.61 |
| Run 1 Stage 2 | 10.0-10.5 | 280 | 2 | 7.9 | 0.35 |
| Run 1 Stage 3 | 10.0 | 282 | 3 | 2.2 | 0.47 |
| (Feed) | — | — | — | 269 | 1.2 |
| Run 2 Stage 1 | 10.0-11.5 | 278 | 1 | 10 | 0.81 |
| Run 2 Stage 2 | 10.0-11.0 | 309 | 2 | 4.8 | 0.51 |
| Run 2 Stage 3 | 10.0-10.5 | 305 | 3 | 1.7 | 0.53 |
| (Feed) | — | — | — | 269 | 1.2 |
| Run 3 Stage 1 | 10.0-11.0 | 342 | 1 | 11 | 0.47 |
| Run 3 Stage 2 | 10.0-11.0 | 335 | 2 | 2.7 | <0.1 |
| Run 3 Stage 3 | 10.0-10.5 | 331 | 3 | 0.7 | 0.1 |

TABLE 6

THE FEED HAVING 269 PPM ETHYLENE OXIDE AND 1.2 PPM DIOXANE IMPURITIES

| Sample No. | Chamber P, mm Hg | Feed ~T,°F. | Stage | EO, ppm | Dioxane, ppm |
|---|---|---|---|---|---|
| (Feed) | — | — | — | 269 | 3.5 |
| Run 1 Stage 1 | 10.0-11.2 | 277 | 1 | 37 | 1.5 |
| Run 1 Stage 2 | 10.0-10.5 | 289 | 2 | 9.8 | 1.3 |
| Run 1 Stage 3 | 10.0-11.0 | 272 | 3 | 4.0 | 1.1 |
| (Feed) | — | — | — | 269 | 3.5 |
| Run 2 Stage 1 | 10.0-12.0 | 305 | 1 | 47 | 1.7 |
| Run 2 Stage 2 | 10.0-11.0 | 308 | 2 | 13 | 1.4 |
| Run 2 Stage 3 | 10.0-10.5 | 302 | 3 | 3.4 | 0.91 |
| (Feed) | — | — | — | 269 | 3.5 |
| Run 3 Stage 1 | 10.0-11.5 | 332 | 1 | 17.3 | 1.4 |
| Run 3 Stage 2 | 10.0-10.5 | 340 | 2 | 4.8 | 0.69 |
| Run 3 Stage 3 | 10.0-10.5 | 335 | 3 | 2.0 | 0.55 |
| (Feed) | — | — | — | 269 | 3.5 |
| Run 4 Stage 1 | 9.5-11.0 | 370 | 1 | 1.4 | 0.19 |
| Run 4 Stage 2 | 9.5-11.0 | 370 | 2 | 0.3 | <0.1 |
| Run 4 Stage 3 | 10.0 | 365 | 3 | 0.1 | <0.1 |

While certain details have been shown for the purpose of illustrating this invention, it will be apparent to those skilled in this art that various changes and modifications may be made herein without departing from the spirit or scope of the invention.

Having described our invention what we desire to secure by letters patent is:

We claim:

1. A process for the purification of liquid alcohol alkoxylate polymer feed streams containing one or more impurities present in a quantity of less than 2% by weight of the stream per impurity comprises:

(a) forcing the feed stream through a spray nozzle into an inert atmosphere at a temperature of from about 68° F. to about 392° F., where the pressure is at or below one atmosphere in such a manner to atomize the feed stream into particulate drops having a size in the range of from about 1,000 microns to about 50 microns in diameter, (b) retaining the particulate drops under the conditions of (a), and within a temperature in the range of from about 68° F. to about 392° F. for at least 0.1 second to form impurity vapors, (c) removing the impurity vapors that form during step (b), and (d) collecting the purified, atomized feed stream liquid wherein the purified feed stream has a vapor pressure no higher than $1\times10^{-3}$ mm of mercury at 68° F., and no higher than 50 mm of mercury at 392° F., and the vapor pressure limits of any impurity removed in step (c) require that its said vapor pressure be no lower than 5,000 mm of mercury at 392° F., and no lower than 10 mm of mercury at 68° F.

2. A process as described in claim 1 wherein, atomization takes place at a temperature in the range of from about 248° F. to about 392° F.

3. A process as described in claim 2 wherein, the feed stream is atomized while pressure is maintained in a range of from about 0.5 mm of Hg (absolute) to about 300 mm of Hg (absolute).

4. A process as described in claim 3 wherein, the impurities removed are selected from the group consisting of: ethylene oxide, propylene oxide, dioxane, water and alcohol.

5. A process as described in claim 4 wherein, the liquid feed stream is a polymer made from one or more monomers at least one of which is selected from the group consisting of: ethylene oxide, and propylene oxide.

6. A process as described in claim 2 wherein, an inert gas purge is maintained at a rate in a range of from about 0.1 to about 100 volumes of gas per volume of feed.

7. A process as described in claim 5 wherein the feed stream is subjected to two or more sequential sprayings.

* * * * *